United States Patent
Kim

(10) Patent No.: US 11,357,485 B2
(45) Date of Patent: Jun. 14, 2022

(54) DEVICE FOR PERFORMING TRICUSPID REGURGITATION OPERATION

(71) Applicant: TAU PNU MEDICAL CO., LTD., Busan (KR)

(72) Inventor: June Hong Kim, Busan (KR)

( * ) Notice: Subject to any disclaimer, the term of this patent is extended or adjusted under 35 U.S.C. 154(b) by 0 days.

(21) Appl. No.: 16/635,141

(22) PCT Filed: Jul. 25, 2018

(86) PCT No.: PCT/KR2018/008409
§ 371 (c)(1),
(2) Date: Jan. 29, 2020

(87) PCT Pub. No.: WO2019/027175
PCT Pub. Date: Feb. 7, 2019

(65) Prior Publication Data
US 2020/0367870 A1 Nov. 26, 2020

(30) Foreign Application Priority Data

Jul. 31, 2017 (KR) .......................... 10-2017-0096829

(51) Int. Cl.
*A61B 17/00* (2006.01)
(52) U.S. Cl.
CPC .............. *A61B 17/00234* (2013.01); *A61B 2017/00243* (2013.01); *A61B 2017/00783* (2013.01)
(58) Field of Classification Search
CPC .... A61B 17/00234; A61B 2017/00243; A61B 2017/00783; A61F 2/24
See application file for complete search history.

(56) References Cited

U.S. PATENT DOCUMENTS

| | | | | |
|---|---|---|---|---|
| 2011/0112632 | A1* | 5/2011 | Chau ..................... | A61F 2/2457 623/2.11 |
| 2011/0257677 | A1* | 10/2011 | Carr, Jr ................... | A61F 2/01 606/200 |
| 2013/0325110 | A1* | 12/2013 | Khalil .................. | A61F 2/2427 623/2.11 |
| 2013/0338763 | A1* | 12/2013 | Rowe ................... | A61F 2/2427 623/2.11 |
| 2015/0366556 | A1* | 12/2015 | Khairkhahan ..... | A61B 17/0401 606/232 |
| 2016/0228246 | A1* | 8/2016 | Zimmerman ........... | A61F 2/246 |

* cited by examiner

Primary Examiner — Robert A Lynch
(74) Attorney, Agent, or Firm — Justin Kim

(57) ABSTRACT

A device for performing tricuspid regurgitation operation is proposed. The device for performing tricuspid regurgitation operation is easily inserted through the inferior vena cava, the tricuspid valve, and the pulmonary artery in sequence in order to treat tricuspid regurgitation (TR) which is a disease where blood from the right ventricle flows back into the right atrium through an empty space (i.e., orifice) formed by incomplete closing of the tricuspid valve (TV) which is positioned between the right atrium and the right ventricle of the heart. The device includes: a fixing member for pulmonary artery installed in the pulmonary artery; a fixing member for inferior vena cava installed in the inferior vena cava; a connecting tube connecting the fixing member for the pulmonary artery and the fixing member for the inferior vena cava to each other; and a blocking part passing obliquely through the tricuspid valve.

13 Claims, 11 Drawing Sheets

[FIG. 1]
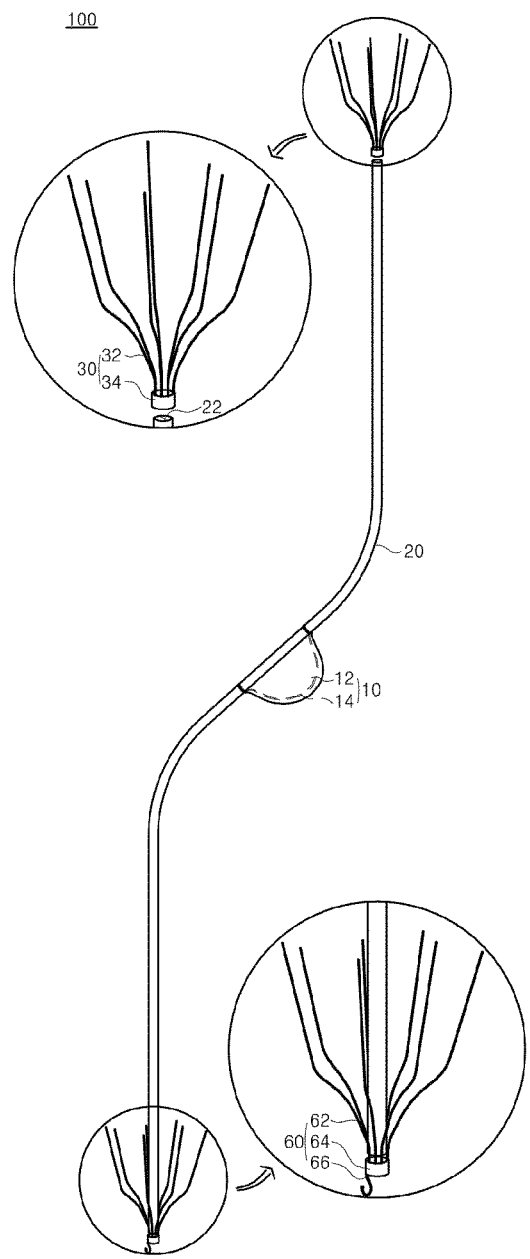

[FIG. 2]
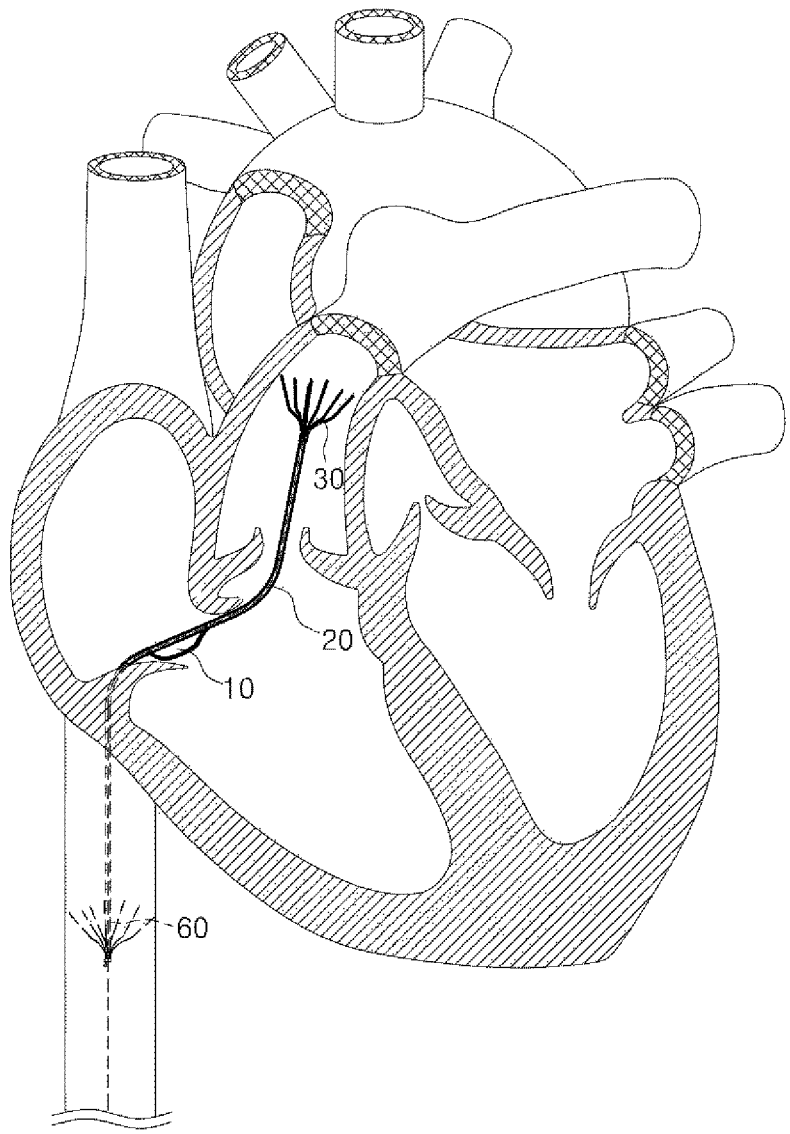

[FIG. 3]
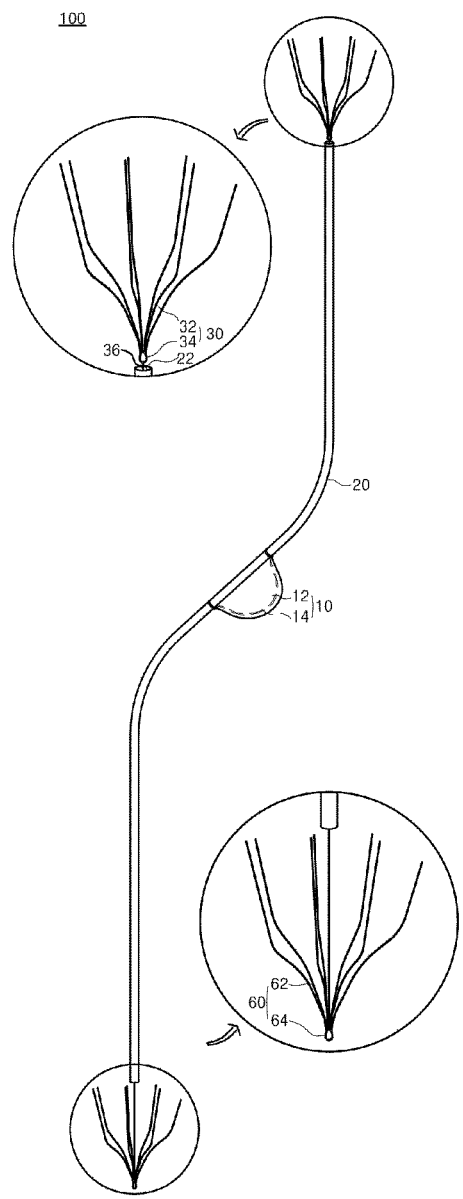

[FIG. 4]
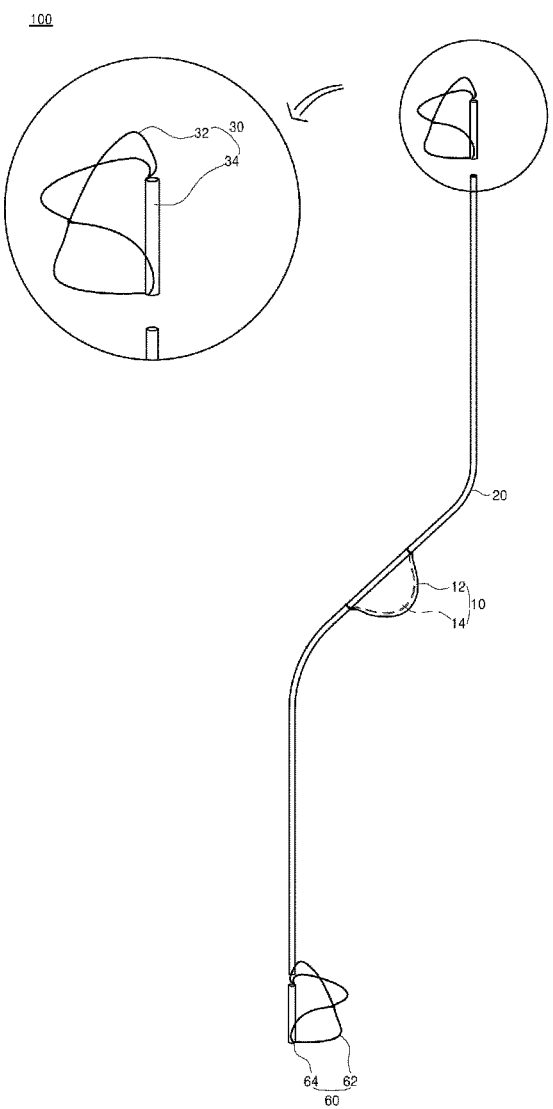

[FIG. 5]
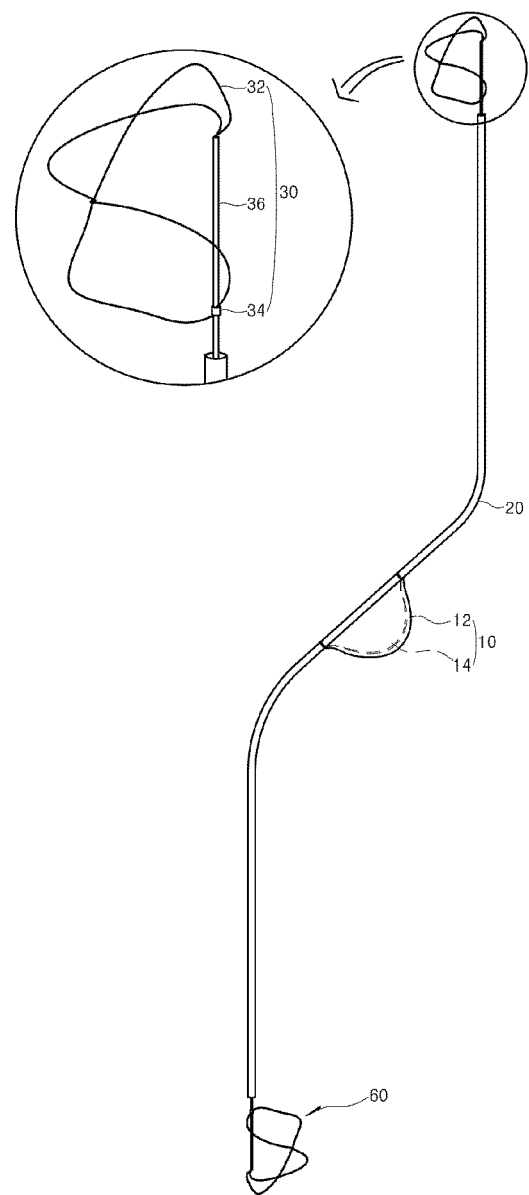

[FIG. 6]
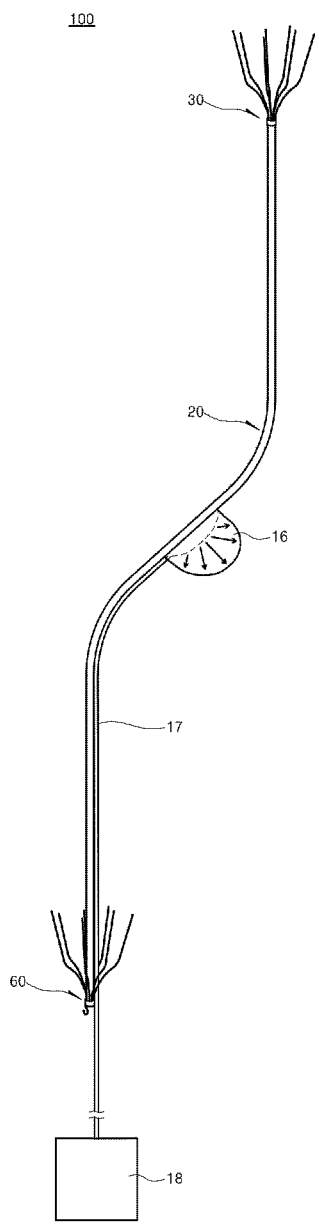

[FIG. 7]
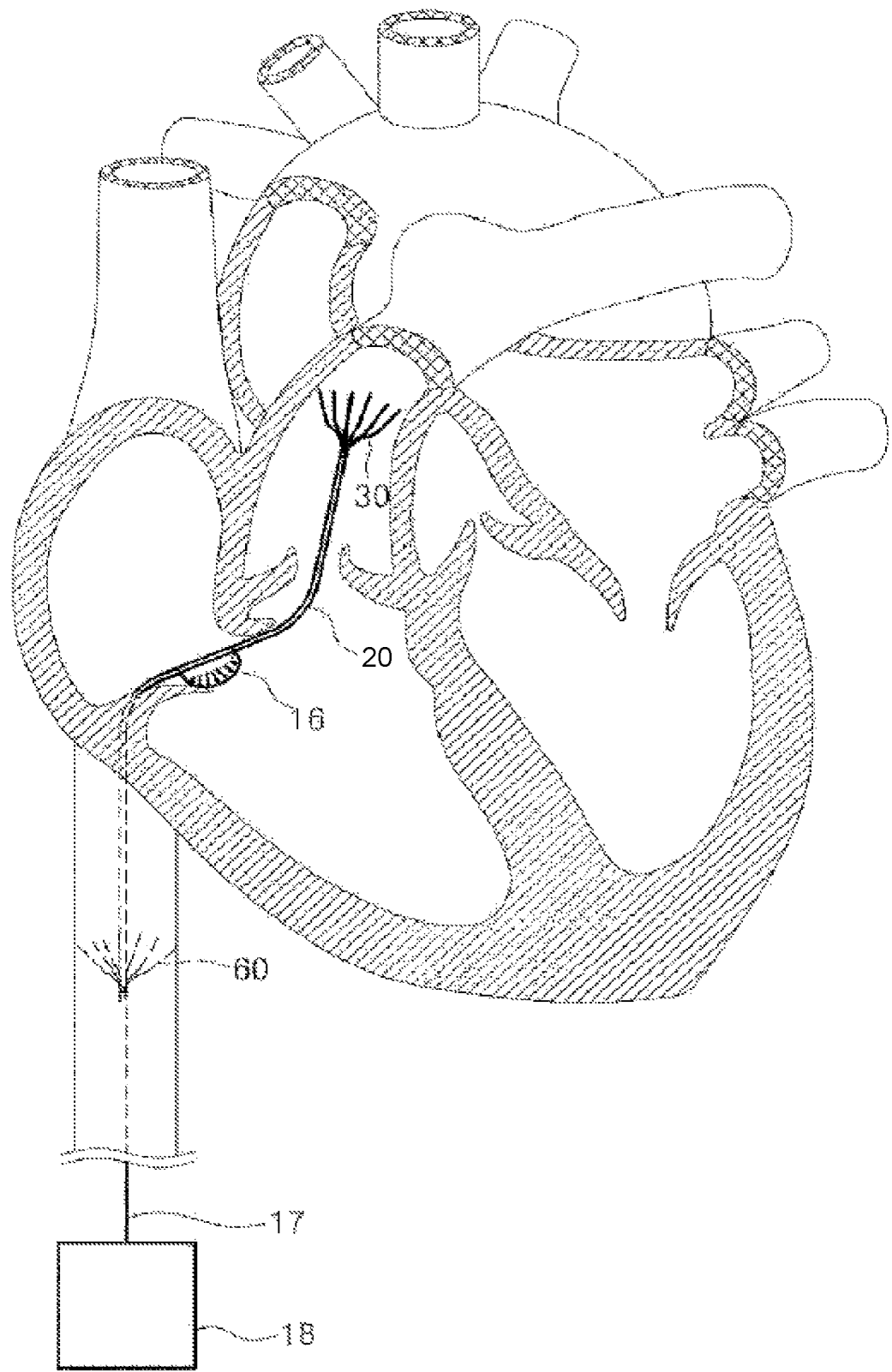

[FIG. 8]
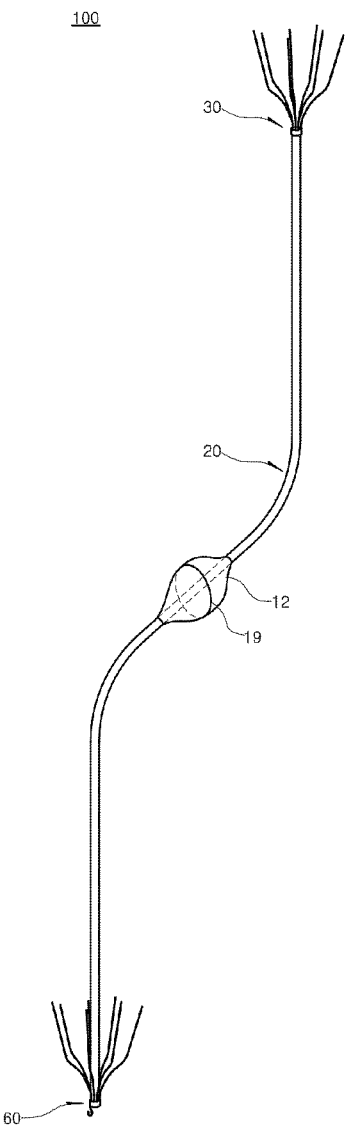

[FIG. 9]
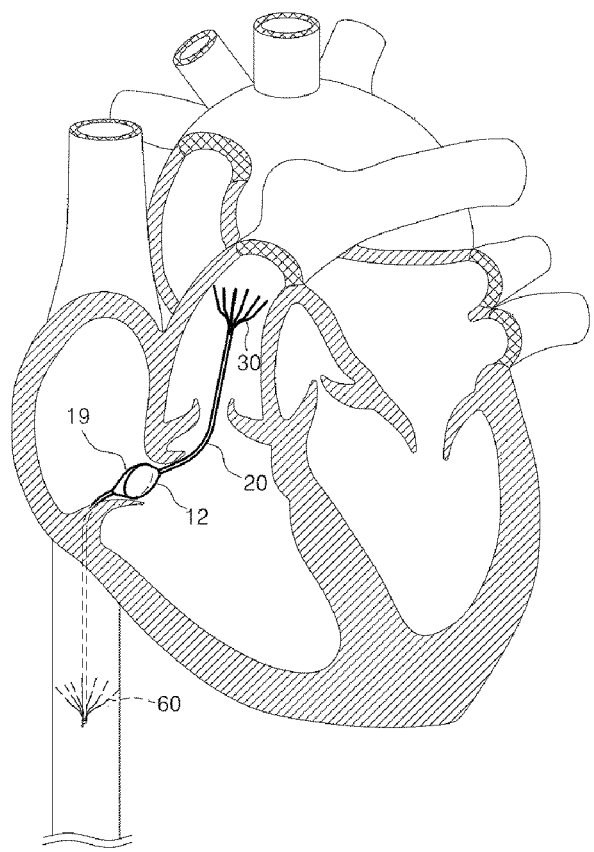

[FIG. 10]
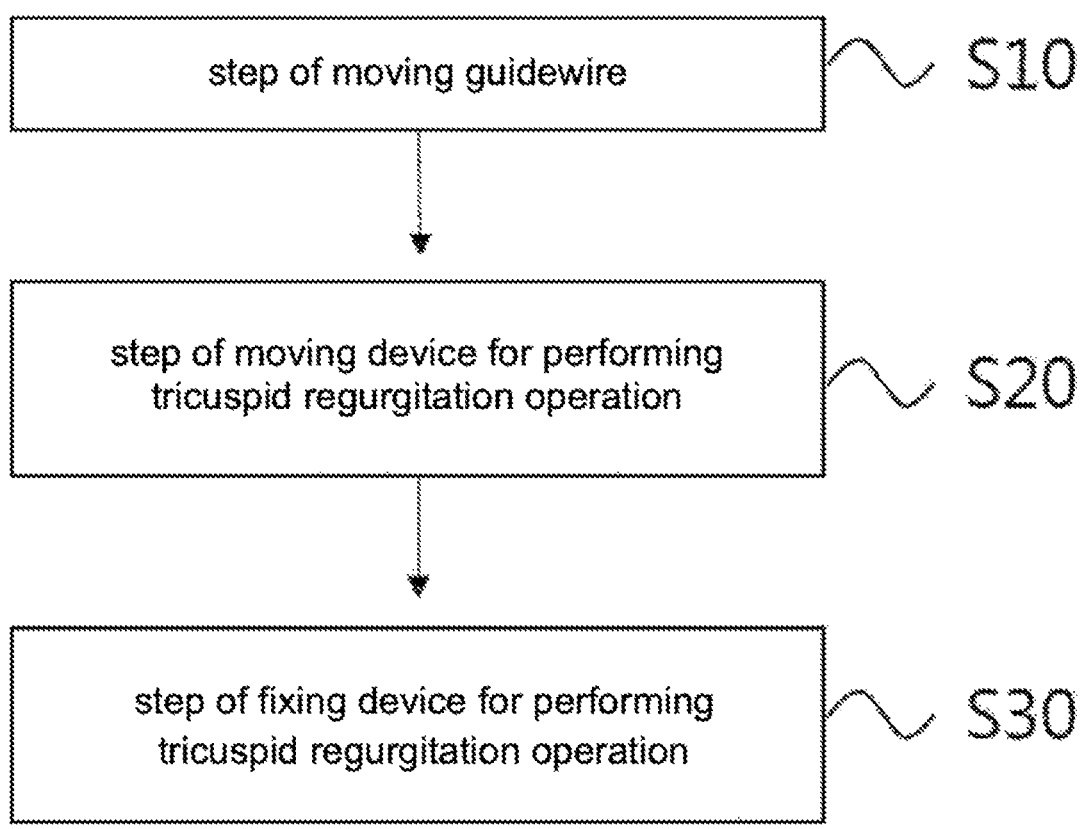

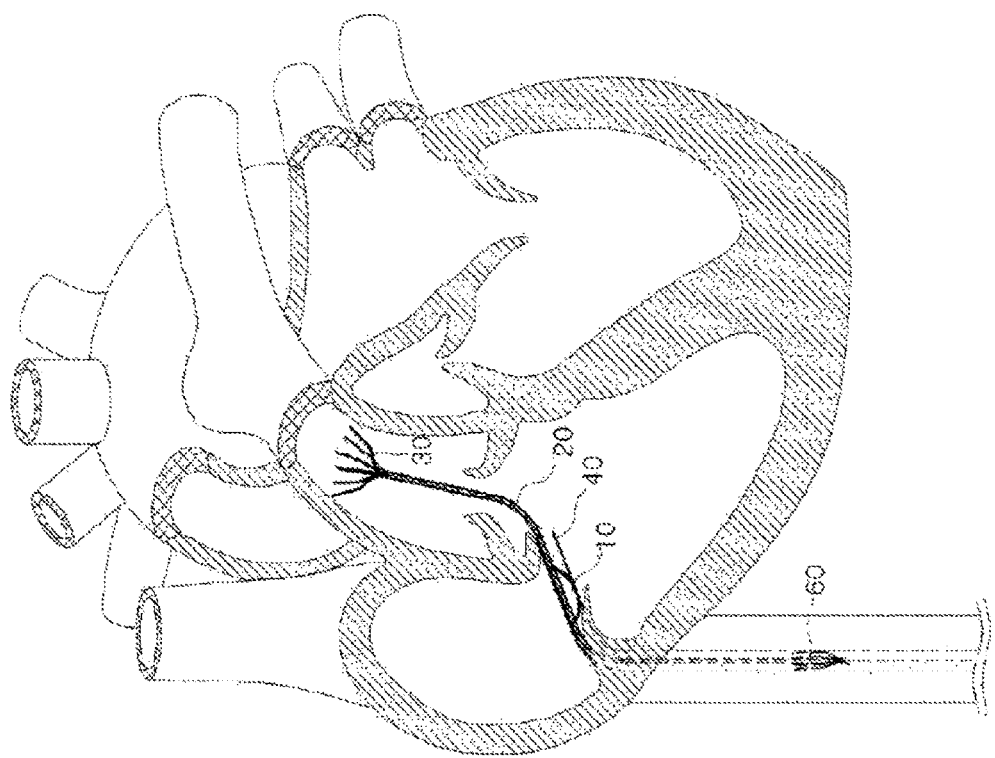
[FIG. 11A]
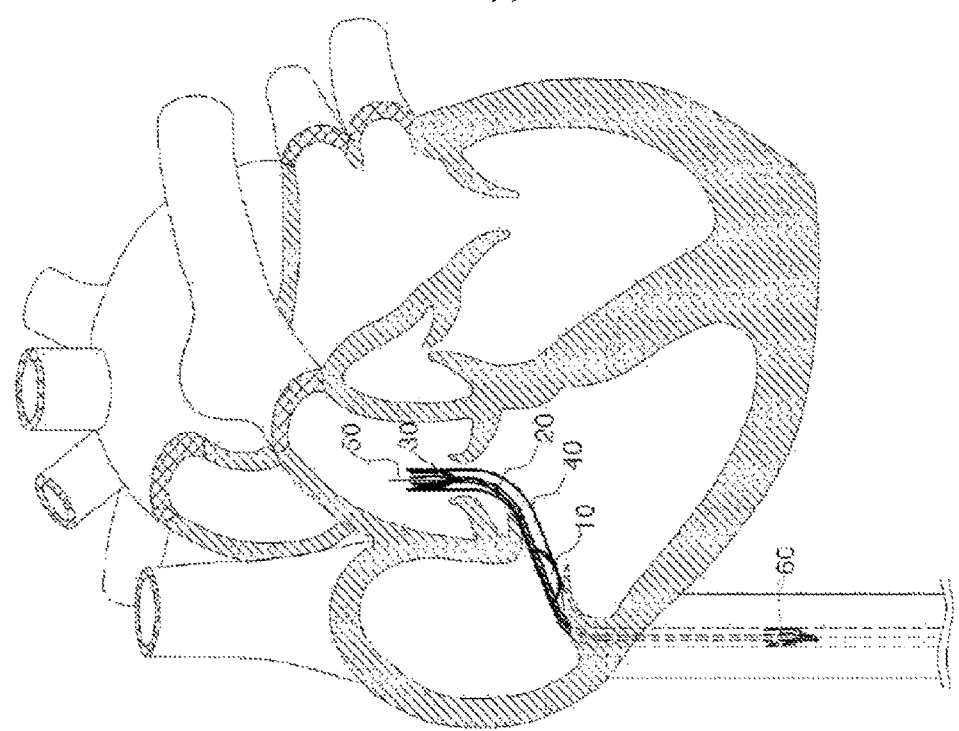
[FIG. 11B]

DEVICE FOR PERFORMING TRICUSPID REGURGITATION OPERATION

TECHNICAL FIELD

The present invention relates to a device for performing tricuspid regurgitation operation. More particularly, the present invention relates to a device for performing tricuspid regurgitation operation, wherein the device is easily inserted through the inferior vena cava, the tricuspid valve, and the pulmonary artery in sequence in order to treat tricuspid regurgitation (TR) which is a disease where blood from the right ventricle flows back into the right atrium through an empty space (i.e., orifice) formed by incomplete closing of the tricuspid valve (TV) which is positioned between the right atrium and the right ventricle of the heart.

BACKGROUND ART

The heart is composed of four hollow chambers: the left atrium, the left ventricle, the right atrium, and the right ventricle, and are respectively connected to the pulmonary vein, the aorta, the vena cava, and the pulmonary artery. There are valves between the ventricles and the atria. The valve between the left atrium and the left ventricle is called the mitral valve, and the valve between the right atrium and the right ventricle is called the tricuspid valve.

The heart repeats contraction and relaxation to enable blood to circulate. In the systolic phase of the heart, blood in the heart moves to blood vessels. The blood in the right ventricle flows to the pulmonary artery, and the blood in the left ventricle flows to the aorta.

However, when a valve is not working properly, blood backflow occurs, thereby causing the blood that normally flows into blood vessels to flow back to an atrium during the heart contraction.

Tricuspid regurgitation (TR) refers to a symptom, wherein an orifice is formed because the tricuspid valve (TV) between the right atrium and the right ventricle is stretched or torn, or because the chordae tendineae holding the tricuspid valve is broken, and thus the tricuspid valve closes incompletely when the tricuspid valve needs to be closed, resulting in blood backflowing from the right ventricle to the right atrium through the orifice during cardiac contraction. This is also called tricuspid valve insufficiency.

U.S. Pat. Nos. 8,486,136 B2, 7,854,762 B2, and 9,474,605 B2 are patents disclosing devices for treating the tricuspid regurgitation, and the devices for treating tricuspid regurgitation are inserted into the superior vena cava, the tricuspid valve, the right ventricle in sequence and block the orifice of the tricuspid valve, thereby treating the tricuspid regurgitation. In the devices for the treatment of the tricuspid regurgitation, an anchor installed at one end of each of the devices is fixed to a ventricle, and the other end thereof is fixed to the outside of the heart by passing through the superior vena cava. Accordingly, the blocking part of the related patents is placed in an unstable state being passed through a centerline of the orifice of the tricuspid valve with a longitudinal orientation and floating within the heart.

The fixing device of the conventional devices for treatment of tricuspid regurgitation is fixed to a ventricle and a position outside the heart. Since the heart is positioned above the diaphragm and the heart moves upward and downward according to the vertical movement of the diaphragm during breathing, the conventional devices for the treatment tricuspid regurgitation move upward and downward according to the movement of the diaphragm during breathing. When this movement is repeated, there occurs a problem in that the blocking part is positioned off the centerline of the orifice of the tricuspid valve. When the blocking part deviates from the centerline of the orifice of the tricuspid valve, the function of the tricuspid valve is adversely affected.

Moreover, in Korean Patent Application Publication No. 10-2017-0044065 invented by the present inventor, a device for performing tricuspid regurgitation operation is disclosed, wherein the device has a blocking part that passes obliquely through the tricuspid valve by connecting the coronary sinus and the ventricular septum to each other. The blocking part is stably positioned inside the heart, but requires a relatively difficult treatment by being passed through the ventricular septum.

DISCLOSURE

Technical Problem

The present invention is to provide a device for performing tricuspid regurgitation operation that may simply treat the tricuspid regurgitation by passing through the inferior vena cava, the tricuspid valve, and the pulmonary artery in sequence to solve the problem of the related art.

In addition, the present invention is to provide a device for performing tricuspid regurgitation operation, wherein a blocking part passes obliquely through an orifice of the tricuspid valve and may stably block the orifice of the tricuspid valve.

In addition, the present invention is to provide a device for performing tricuspid regurgitation operation that is configured to easily maintain a centerline orientation of an orifice of the tricuspid valve without being affected by the movement of the diaphragm during breathing, by fixing the fixing members to the pulmonary artery and the inferior vena cava respectively.

The objectives of the present invention are not limited to the above-mentioned objectives, and other objectives that are not mentioned will be clearly understood by those skilled in the art from the following description.

Technical Solution

In order to achieve the objectives of the present invention, there is provided a device for performing tricuspid regurgitation operation, the device including:
a fixing member for the pulmonary artery installed in the pulmonary artery; a fixing member for the inferior vena cava installed in the inferior vena cava; a connecting tube connecting the fixing member for the pulmonary artery and the fixing member for the inferior vena cava to each other; and a blocking part passing obliquely through the tricuspid valve.

The connecting tube may be provided with a guidewire-guiding lumen formed therein to be movable along a guidewire.

The fixing member for the pulmonary artery may include at a lower part thereof: a fixing member body for the pulmonary artery; and a plurality of fixtures for the pulmonary artery radially coupled to the fixing member body for the pulmonary artery, and the fixing member for the inferior vena cava may include at a lower part thereof: a fixing member body for the inferior vena cava; and a plurality of fixtures for the inferior vena cava radially coupled to the fixing member body for the inferior vena cava.

The fixing member body for the pulmonary artery or the fixing member body for the inferior vena cava may be configured in a cylindrical shape having a hole in a central axis thereof and coupled to the connecting tube.

The fixing member body for the inferior vena cava may include a protruding hook for the inferior vena cava, the protruding hook being coupled to a lower surface of the fixing member body for the inferior vena cava and capable of being hooked by using a hook inserted from outside.

The fixing member body for the pulmonary artery or the fixing member body for the inferior vena cava may be configured in a ring shape, and the fixing member for the pulmonary artery or the fixing member for the inferior vena cava may include a fixing-member-connecting wire having a first end thereof coupled to the fixing member body for the pulmonary artery and inserted into the connecting tube, and having a second end thereof coupled to the fixing member body for the inferior vena cava.

The fixing member for the pulmonary artery may include: a fixture for the pulmonary artery formed of a wire having a ribbon shape; and a fixing member body for the pulmonary artery coupled to one end of the fixture for the pulmonary artery, and the fixing member for the inferior vena cava may include: a fixture for the inferior vena cava formed of the wire having the ribbon shape; and a fixing member body for the inferior vena cava coupled to one end of the fixture for the inferior vena cava.

The fixing member body for the pulmonary artery or the fixing member body for the inferior vena cava may be configured in a cylindrical shape having a hole in a central axis thereof and coupled to the connecting tube.

The fixing member body for the pulmonary artery or the fixing member body for the inferior vena cava may be configured in a ring shape, and the fixing member for the pulmonary artery or the fixing member for the inferior vena cava may include a fixing-member-connecting wire having a first end thereof coupled to the fixing member for the pulmonary artery and inserted into the connecting tube, and having a second end thereof coupled to the fixing member for the inferior vena cava.

The blocking part may include: a supporting wire having both ends thereof coupled to the connecting tube; and a blocking membrane having one side thereof fixed to the connecting tube and supported by the supporting wire.

The blocking part may be a blocking balloon in a balloon shape capable of expanding or contracting, and the blocking part further may include: a balloon tube having a first end thereof connected to and communicated with the blocking balloon; and a balloon-adjusting hub connected to a second end of the balloon tube and installed outside a patient's body, the balloon-adjusting hub expanding or contracting the blocking balloon.

The blocking part may include: a ring-shaped wire installed to make the connecting tube to be passed through thereof and having a central axis thereof obliquely formed with respect to the connecting tube; and a blocking membrane connecting the connecting tube and the ring-shaped wire to each other.

The device for performing tricuspid regurgitation operation may further include a sheath tube formed with a lumen into which the device for performing tricuspid regurgitation operation may be inserted to move into a patient's body.

Advantageous Effects

A device for performing tricuspid regurgitation operation according to the present invention may pass through the inferior vena cava, the tricuspid valve, and the pulmonary artery in sequence, so that placement of a blocking part in an orifice of the tricuspid valve is relatively simple and the treatment time is short.

In addition, the blocking part may pass obliquely through a centerline of the orifice of the tricuspid valve to stably block the orifice of the tricuspid valve.

In addition, fixing members are fixed to the pulmonary artery and the inferior vena cava so that the position of the blocking part passing through the centerline of the orifice of the tricuspid valve is not affected by the movement of the diaphragm during breathing.

In addition, since the blocking part of the device for performing tricuspid regurgitation operation according to the present invention is positioned on about the same planar surface as the tricuspid valve, the blocking part has little interaction with the chordae tendineae or the papillary muscles, which are the substructure of the tricuspid valve, thereby having no possibility of causing problems due to the interaction.

DESCRIPTION OF DRAWINGS

FIG. 1 is a perspective view of a device for performing tricuspid regurgitation operation according to a preferred exemplary embodiment of the present invention.

FIG. 2 is a perspective cross-sectional view for describing a state after the treatment using the device for performing tricuspid regurgitation operation of FIG. 1.

FIG. 3 is a perspective view showing another exemplary embodiment of a fixing member for the pulmonary artery and a fixing member for the inferior vena cava in a device for performing tricuspid regurgitation operation of FIG. 1.

FIG. 4 is a perspective view showing yet another exemplary embodiment of a fixing member for the pulmonary artery and a fixing member for the inferior vena cava in a device for performing tricuspid regurgitation operation of FIG. 1.

FIG. 5 is the perspective view showing the yet another exemplary embodiment of the fixing member for the pulmonary artery and the fixing member for the inferior vena cava in the device for performing tricuspid regurgitation operation of FIG. 1.

FIG. 6 is a perspective view of a device for performing tricuspid regurgitation operation according to another preferred exemplary embodiment of the present invention.

FIG. 7 is a perspective cross-sectional view for describing a state after the treatment using the device for performing tricuspid regurgitation operation of FIG. 6.

FIG. 8 is a perspective view of a device for performing tricuspid regurgitation operation according to yet another preferred exemplary embodiment of the present invention.

FIG. 9 is a perspective cross-sectional view for describing a state after the treatment using the device for performing tricuspid regurgitation operation of FIG. 8.

FIG. 10 is a flowchart showing steps of the treatment of tricuspid regurgitation by using the device for performing tricuspid regurgitation operation of the present invention.

FIGS. 11A and 11B are perspective cross-sectional views for describing a principle of treating tricuspid regurgitation by using the device for performing tricuspid regurgitation operation of the present invention.

DESCRIPTION OF THE REFERENCE NUMERALS IN THE DRAWINGS

14: supporting wire, 10: blocking part, 12: blocking membrane

16: blocking balloon
17: balloon tube
18: balloon-adjusting hub
19: ring-shaped wire
20: connecting tube
22: guidewire-guiding lumen
30: fixing member for the pulmonary artery
32: fixture for the pulmonary artery
34: fixing member body for the pulmonary artery
36: fixing-member-connecting wire
40: sheath tube
50: guidewire
60: fixing member for the inferior vena cava
62: fixture for the inferior vena cava
64: fixing member body for the inferior vena cava
66: protruding hook for the inferior vena cava
100: device for performing tricuspid regurgitation operation
S10: step of moving guidewire
S20: step of moving device for performing tricuspid regurgitation operation
S30: step of fixing device for performing tricuspid regurgitation operation

BEST MODE

Benefits and features of the present invention, and methods of accomplishing the same may be understood more readily by reference to the following detailed description of exemplary embodiments and the accompanying drawings. However, the present disclosure may be embodied in many different forms, and should not be construed as being limited to the exemplary embodiments set forth herein. Rather, these exemplary embodiments are provided so that this disclosure will be thorough and complete and will fully convey the concept of the invention to those skilled in the art, and the present disclosure will only be defined by the appended claims.

Hereinafter, exemplary embodiments of the present invention will be described in detail with reference to the accompanying drawings. Regardless of the drawings, the same reference numbers refer to the same components, and "and/or" includes each and every combination of one or more of the items mentioned.

The terminology used herein is for the purpose of describing particular embodiments only and is not intended to be limiting of the invention. In this description, the singular also includes the plural unless specifically stated otherwise in the phrase. As used herein, "comprises" and/or "comprising" does not exclude the presence or addition of one or more other components in addition to the mentioned components.

Unless otherwise defined, all terms (including technical and scientific terms) used in the present description may be used in a sense that can be commonly understood by those skilled in the art. In addition, the terms defined in the commonly used dictionaries are not comprehensively or excessively interpreted unless they are specifically defined clearly.

Hereinafter, preferred exemplary embodiments of the present invention will be described in detail with reference to the accompanying drawings.

FIG. 1 is a perspective view of a device for performing tricuspid regurgitation operation according to a preferred exemplary embodiment of the present invention.

Referring to FIG. 1, the device for performing tricuspid regurgitation operation 100 according to the present invention fundamentally includes a fixing member for the pulmonary artery 30, a fixing member for the inferior vena cava 60, a connecting tube 20, and a blocking part 10.

The fixing member for the pulmonary artery 30 is fixed to the pulmonary artery and includes: at the lower part thereof, a fixing member body for the pulmonary artery 34; and a plurality of fixtures for the pulmonary artery 32 radially coupled on the upper surface of the fixing member body for the pulmonary artery 34.

The fixing member for the inferior vena cava 60 is fixed to the inferior vena cava and includes: at the lower part thereof, a fixing member body for the inferior vena cava 64; a plurality of fixtures for the inferior vena cava 62 radially coupled to the upper surface of the fixing member body for the inferior vena cava 64; and a protruding hook for the inferior vena cava 66 provided at a position on the lower surface of the fixing member body for the inferior vena cava 64.

The fixture for the pulmonary artery 32 and the fixture for the inferior vena cava 62 may be made of a metal wire (i.e., stainless steel, nylon coating on metal, etc.), and is composed of a shape memory alloy, an elastic body, or a self-expandable stent.

The fixing member body for the pulmonary artery 34 and the fixing member body for the inferior vena cava 64 are configured in a cylindrical shape having a hole formed on a central axis thereof and have an inner circumferential surface closely coupled to an outer circumferential surface of the connecting tube 20.

The connecting tube 20 is provided with a guidewire-guiding lumen 22 formed therein to be movable along a guidewire 50.

The connecting tube 20 may be composed of synthetic resin such as rubber, soft plastic, and the like having softness and high ductility and made of a material having excellent flexibility and resilience to be movable according to the heartbeat.

The fixing member for the pulmonary artery 30 and the fixing member for the inferior vena cava 60 are installed in the same direction. One end of the connecting tube 20 is fitted to the lower side of the fixing member body for the pulmonary artery 34, and the other end of the connecting tube 20 is fitted to the upper side of the fixing member body for the inferior vena cava 64.

In addition to that shown in FIG. 1, it is apparent that the fixing member for the pulmonary artery 30 and the fixing member for the inferior vena cava 60 may be fitted to the connecting tube 20, regardless of distinguishing the upper side or the lower side thereof.

The protruding hook for the inferior vena cava 66 can easily remove the device for performing tricuspid regurgitation operation 100 in the case when the device is needed to be removed from a patient's body. More particularly, in order to remove the device for performing tricuspid regurgitation operation 100, by inserting a wire (not shown) having a hook shape at the upper end thereof to hook and pull the protruding hook for the inferior vena cava 66, the device for performing tricuspid regurgitation operation 100 may be easily removed from the patient's body.

The device for performing tricuspid regurgitation operation 100 further includes a sheath tube 40 having a lumen formed therein to move into the patient's body. Each of the fixing member for the pulmonary artery 30 and the fixing member for the inferior vena cava 60 is inserted into the sheath tube 40 in a folded state when moved into the patient's body, is returned to its original state and unfolded in a radial manner when the sheath tube 40 is removed, and is respectively fixed to the pulmonary artery and the inferior vena cava. The device for performing tricuspid regurgitation operation 100 will be described in detail with reference to FIGS. 10 and 11.

The blocking part 10 is a part that blocks an orifice formed due to incomplete closing of the tricuspid valve, is coupled to one side of the connecting tube 20, and is inserted obliquely into the tricuspid valve.

The blocking part 10 is made of a blocking membrane 12 or a blocking balloon 16, and the like. In FIG. 1, the blocking membrane 12 is illustrated. The blocking membrane 12 has softness, but is not easily torn, and is made of a material suitable for human body such as medical polyurethane, polyolefin, silicone, e-PTFE, PTFE, and the like.

The blocking part 10 includes a supporting wire 14 for holding the shape of the blocking membrane 12. In FIG. 1, both ends of the supporting wire 14 are fixed to the connecting tube 20, but are not necessarily limited thereto, and it is apparent that neither both sides nor one side of the supporting wire 14 may not be fixed to the connecting tube 20.

As shown in FIG. 1, the blocking membrane 12 may have a circular shape as well as a semi-circular shape, and a plurality of connecting tubes 20 may also be installed to adjust the position or to fix the shape of the blocking membrane 12 having the circular shape.

In addition, the material of the supporting wire 14 may be a synthetic resin wire such as nylon or a metal wire (i.e., stainless steel, nylon coating on metal), and the like. The supporting wire 14 may be a single wire, and may also be a form of wire made by twisting a plurality of thin wires.

The blocking membrane 12 may connect the connecting tube 20 and the supporting wire 14 to each other in one layer, but the blocking membrane 12 may be in two layers and configured to be a form where the supporting wire 14 is inserted into the blocking membrane 12.

FIG. 2 is a perspective cross-sectional view for describing a state after the treatment using the device for performing tricuspid regurgitation operation of FIG. 1.

Referring to FIG. 2, a state is illustrated, wherein the device for performing tricuspid regurgitation operation 100 according to the preferred exemplary embodiment of the present invention is inserted into the heart of the patient. To fix the device for performing tricuspid regurgitation operation 100, the fixing member for the pulmonary artery 30 is installed in the pulmonary artery, and the fixing member for the inferior vena cava 60 is installed in the inferior vena cava. The blocking part 10 passes obliquely through the orifice of the tricuspid valve to block the orifice to treat the tricuspid regurgitation.

Therefore, the device for performing tricuspid regurgitation operation 100 according to the present invention may be moved through the inferior vena cava, the tricuspid valve, and the pulmonary artery in sequence to position the blocking part 10 in the orifice of the tricuspid valve. Also, the blocking part 10 may be passed obliquely through the orifice of the tricuspid valve so as to stably block the orifice of the tricuspid valve. In addition, the fixing member for the pulmonary artery 30 and the fixing member for the inferior vena cava 60 are respectively fixed to the pulmonary artery and the inferior vena cava. Accordingly, the blocking part is not affected by the movement of the diaphragm during breathing, so the positional change of the blocking part is less likely to happen even as time passes.

FIG. 3 is a perspective view showing another exemplary embodiment of a fixing member for the pulmonary artery and a fixing member for the inferior vena cava in a device for performing tricuspid regurgitation operation of FIG. 1.

Referring to FIG. 3, at each of the lower parts, the fixing member for the pulmonary artery 30 and the fixing member for the inferior vena cava 60 includes: a fixing member body for the pulmonary artery 34 and a fixing member body for the inferior vena cava 64; and a plurality of fixtures for the pulmonary artery 32 and a plurality of fixtures for the inferior vena cava 62, respectively coupled in a radial shape to the fixing member body for the pulmonary artery 34 and the fixing member body for the inferior vena cava 64. In addition, the fixing member for the pulmonary artery 30 includes the fixing-member-connecting wire 36 for connecting the fixing member for the pulmonary artery 30 and the fixing member for the inferior vena cava 60 to each other. The connecting tube 20 and the blocking part 10 are the same as those in FIG. 1.

The fixing member body for the pulmonary artery 34 and the fixing member body for the inferior vena cava 64 are formed in a ring shape. One end of the fixing-member-connecting wire 36 is coupled to the fixing member body for the pulmonary artery 34 and inserted into the connecting tube 20, and the other end thereof is coupled to the fixing member body for the inferior vena cava 64. The fixing-member-connecting wire 36 may be made of the same material as the supporting wire 42.

Each of the fixing member for the pulmonary artery 30 and the fixing member for the inferior vena cava 60 is inserted in a folded state when inserted into the sheath tube 40 in order to be moved into the patient's body, and is returned to its original state and unfolded in a radial manner when the sheath tube 40 is removed, and then, is respectively fixed to the pulmonary artery and the inferior vena cava.

In this case, the fixture for the pulmonary artery 32 and the fixture for the inferior vena cava 62 may not be inserted into the sheath tube 40, but may be inserted into the connecting tube 20.

FIG. 4 is a perspective view showing yet another exemplary embodiment of a fixing member for the pulmonary artery and a fixing member for the inferior vena cava in a device for performing tricuspid regurgitation operation of FIG. 1.

Referring to FIG. 4, yet another fixing member for the pulmonary artery 30 and fixing member for the inferior vena cava 60 includes: a fixture for the pulmonary artery 32 and a fixture for the inferior vena cava 62, respectively formed of a wire having a ribbon shape with a convex central part; and the fixing member body for the pulmonary artery 34 and the fixing member body for the inferior vena cava 64, respectively coupled to one end of the fixture for the pulmonary artery 32 and the fixture for the inferior vena cava 62. The connecting tube 20 and the blocking part 10 are the same as those in FIG. 1.

The fixing member body for the pulmonary artery 34 and the fixing member body for the inferior vena cava 64 are configured in a cylindrical shape having a hole in a central axis thereof, and each have an inner circumferential surface closely coupled to the outer circumferential surface of the connecting tube 20.

The fixture for the pulmonary artery 32 and the fixture for the inferior vena cava 62, respectively formed of a wire having a convex ribbon shape, may be made of a shape memory alloy, an elastic body, or a self-expanding stent. The fixing member body for the pulmonary artery 34 is fitted to one end of the connecting tube 20, and the fixing member body for the inferior vena cava 64 is fitted to the other end of the connecting tube 20.

The device for performing tricuspid regurgitation operation 100 of FIG. 4 is inserted into the sheath tube 40 when moved into the patient's body. Also, the fixture for the pulmonary artery 32 and the fixture for the inferior vena cava 62 are inserted with the convex center pressed in so as to be inserted into the sheath tube 40, and when the sheath tube 40 is removed, each fixture is returned to the ribbon shape having the convex central part and respectively fixed to the pulmonary artery and the inferior vena cava.

FIG. 5 is a perspective view showing the yet another exemplary embodiment of the fixing member for the pulmonary artery and the fixing member for the inferior vena cava in the device for performing tricuspid regurgitation operation of FIG. 1.

Referring to FIG. 5, the fixing member for the pulmonary artery 30 and fixing member for the inferior vena cava 60 includes: a fixture for the pulmonary artery 32 and an fixture for the inferior vena cava 62, respectively formed of a wire having a ribbon shape with a convex central part; and a fixing member body for the pulmonary artery 34 and a fixing member body for the inferior vena cava 64, respectively having a ring shape and respectively coupled to one end of the fixture for the pulmonary artery 32 and one end of the fixture for the inferior vena cava 62. In addition, the fixing member for the pulmonary artery 30 includes the fixing-member-connecting wire 36 for connecting the fixing member for the pulmonary artery 30 and the fixing member for the inferior vena cava 60 to each other.

In addition, as one end of the fixing-member-connecting wire 36 is coupled to the fixture for the pulmonary artery 32 and inserted into the connecting tube 20 by passing through the central axis of the fixing member body for the pulmonary artery 34, the other end thereof passes through the central axis of the fixing member body for the inferior vena cava 64 and is coupled to the fixture for the inferior vena cava 62. The connecting tube 20 and the blocking part 10 are the same as those in FIG. 1.

The fixture for the pulmonary artery 32 and the fixture for the inferior vena cava 62 are inserted in a flat ribbon shape into the sheath tube 40 in order to be moved into the patient's body. When the sheath tube 40 is removed, the fixing member body for the pulmonary artery 34 and the fixing member body for the inferior vena cava 64, or the fixture for the pulmonary artery 32 and the fixture for the inferior vena cava 62 are pushed forward by the sheath tube 40. Accordingly, the fixture for the pulmonary artery 32 and the fixture for the inferior vena cava 62 become a ribbon shape having a convex central part, and are respectively fixed to the pulmonary artery and the inferior vena cava.

In this case, the fixture for the pulmonary artery 32 and the fixture for the inferior vena cava 62 may not be inserted into the sheath tube 40, but may be inserted into the connecting tube 20.

Different forms other than the fixing member for the pulmonary artery 30 and the fixing member for the inferior vena cava 60 of the above-described form are also possible.

FIG. 6 is a perspective view of a device for performing tricuspid regurgitation operation according to another preferred exemplary embodiment of the present invention, and FIG. 7 is a perspective cross-sectional view for describing a state after the treatment using the device for performing tricuspid regurgitation operation of FIG. 6.

Referring to FIGS. 6 and 7, the device for performing tricuspid regurgitation operation 100 according to the another preferred exemplary embodiment of the present invention includes: the fixing member for the pulmonary artery 30 fixed to the pulmonary artery; the fixing member for the inferior vena cava 60 fixed to the inferior vena cava; the connecting tube 20 connecting the fixing member for the pulmonary artery 30 and the fixing member for the inferior vena cava 60 to each other; and the blocking part 10 coupled to one side of the connecting tube 20.

The blocking part 10 includes: a blocking balloon 16 having a balloon shape capable of expanding or contracting; a balloon tube 17 having one end thereof coupled to and communicated with the blocking balloon 16; and a balloon-adjusting hub 18 having the other end thereof coupled to the balloon tube 17 and supplying air, oxygen, foam, and the like to the blocking balloon 16.

The balloon-adjusting hub 18 is installed outside the patient's body, and the blocking balloon 16 may be expanded or contracted by air, oxygen, foam, and the like supplied from the balloon-adjusting hub 18.

The blocking balloon 16 is expanded by receiving air, oxygen, form, and the like from the balloon-adjusting hub 18 so as to block the orifice of the tricuspid valve, and the size of the blocking balloon 16 is adjustable according to the size of the orifice.

The fixing member for the pulmonary artery 30 and the fixing member for the inferior vena cava 60 may be of the form described above with reference to FIGS. 3 to 5 as well as the form shown in FIGS. 6 and 7.

FIG. 8 is a perspective view of a device for performing tricuspid regurgitation operation according to yet another preferred exemplary embodiment of the present invention, and FIG. 9 is a perspective cross-sectional view for describing a state after the treatment using the device for performing tricuspid regurgitation operation of FIG. 8.

Referring to FIGS. 8 and 9, the device for performing tricuspid regurgitation operation 100 according to the yet another preferred exemplary embodiment of the present invention includes: the fixing member for the pulmonary artery 30 fixed to the pulmonary artery; the fixing member for the inferior vena cava 60 fixed to the inferior vena cava; the connecting tube 20 connecting the fixing member for the pulmonary artery 30 and the fixing member for the inferior vena cava 60 to each other; and the blocking part 10 coupled to an outer circumferential surface of the connecting tube 20.

The fixing member for the pulmonary artery 30 and the fixing member for the inferior vena cava 60 may be of the form described above with reference to FIGS. 3 to 5 as well as the form shown in FIGS. 8 and 9.

The blocking part 10 is installed so that the connecting tube 20 passes through thereof, and includes a ring-shaped wire 19 having a central axis obliquely formed on the connecting tube 20, and a blocking membrane 41 connecting the connecting tube 20 and the ring-shaped wire 19 to each other.

The ring-shaped wire 19 is positioned in parallel to the tricuspid valve inclined at a certain angle, due to a central axis obliquely formed to the connecting tube 20. Thus, the orifice of the tricuspid valve may be effectively blocked.

Hereinafter, a process of treating tricuspid regurgitation using the device for performing tricuspid regurgitation operation 100 will be described.

FIG. 10 is a flow chart showing the treatment steps using the device for performing tricuspid regurgitation operation of the present invention, and FIG. 11 is a perspective cross-sectional view for describing a principle of treating tricuspid regurgitation by using the device for performing tricuspid regurgitation operation of the present invention.

Referring to FIGS. 10 and 11, there are steps including: a step of moving guidewire S10; a step of moving device for performing tricuspid regurgitation operation S20; and a step of fixing device for performing tricuspid regurgitation operation S30. In addition, in order to move easily inside the patient's body, the device for performing tricuspid regurgitation operation 100 of the present invention further includes the guidewire 50 and the sheath tube 40.

The step of moving guidewire S10 is a step of inserting the guidewire 50 into the inferior vena cava, the tricuspid valve, and the pulmonary artery in sequence so that the device for performing tricuspid regurgitation operation 100 of the present invention may easily move into the patient's body. The movements of the wire and catheter in the patient's body may be observed through X-rays. In order for the guidewire 50 to safely pass through the tricuspid valve, a guidewire-guiding tube (not shown) having a lumen formed therein is additionally required. The guidewire-guiding tube (not shown) has a balloon or a pigtail-shaped locking means provided at the upper end thereof to pass through the safe zone of the tricuspid valve. The safe zone refers to a space free of leaflets of the tricuspid valve, subvalvular structures such as the chordae tendineae and the papillary muscles of the tricuspid valve, and the modulator band. The balloon or the pigtail-shaped locking means prevents the guidewire-guiding tube from being moved forward by being caught in the subvalvular structures and the moderator band when moving out of the safe zone. Therefore, the guidewire-guiding tube (not shown) is moved to the inferior vena cava, the safe zone of the tricuspid valve, and the pulmonary artery in sequence and the guidewire 50 is inserted into the guidewire-guiding tube and moves. When one end of the guidewire 50 moves up to the pulmonary artery, the guidewire-guiding tube is removed out of the patient's body. At this time, the device for performing tricuspid regurgitation operation 100 is inserted into the sheath tube 40, and is prepared to move into the patient's body. The fixture for the pulmonary artery 32 and the fixture for the inferior vena cava 62 are inserted into the sheath tube 40 in a folded state, and the blocking part 10 is inserted into the sheath tube 40 in a wound state on the outer circumferential surface of the connecting tube 20.

The step of moving device for performing tricuspid regurgitation operation S20 is a step of moving the device for performing tricuspid regurgitation operation 100 into the patient's body by inserting the guidewire 50 into the guidewire-guiding lumen 22 formed in the sheath tube 40. The device for performing tricuspid regurgitation operation 100 inserted into the sheath tube 40 along the path where the guidewire 50 is inserted (i.e., the inferior vena cava, the tricuspid valve, and the pulmonary artery in sequence) is inserted into the patient's body. Once being positioned in the orifice of the tricuspid valve, the movement stops.

The step of fixing device for performing tricuspid regurgitation operation S30 is a step of removing the guidewire 50 and the sheath tube 40 so as to fix the device for performing tricuspid regurgitation operation 100 to the pulmonary artery and the inferior vena cava. When the blocking part 10 is positioned by passing obliquely through the orifice of the tricuspid valve, the guidewire 50 is removed out of the patient's body. In addition, when the sheath tube 40 is also removed out of the patient's body, the fixture for the pulmonary artery 32 and the fixture for the inferior vena cava 62, respectively formed of a shape memory alloy, an elastic body, or a self-expanding stent, are returned to the radial form, and thus the fixing member for the pulmonary artery 30 is fixed to the pulmonary artery and the fixing member for the inferior vena cava 60 is fixed to the inferior vena cava. In addition, the blocking part 10, which is inserted into the sheath tube 40 in a wound state, is also returned to its original state, thereby treating tricuspid regurgitation by blocking the orifice formed by incomplete closing of the tricuspid valve.

Although the exemplary embodiment of the present invention have been described above with reference to the accompanying drawings, it will be understood that those skilled in the art to which the present invention pertains may implement the present invention in other specific forms without departing from the technical spirit or essential features thereof. Therefore, the exemplary embodiments described above are to be understood in all respects as illustrative and not restrictive.

The invention claimed is:

1. A catheter device comprising:
   a connecting tube having a proximal segment, a distal segment, and a middle segment between the proximal and distal segments;
   a blocking part mounted on the middle segment of the connecting tube;
   a distal fixing member for anchoring within a pulmonary artery, wherein the distal fixing member is at a distal end of the distal segment of the connecting tube, wherein optionally, the distal fixing member comprises a pre-determined natural bend;
   a proximal fixing member for anchoring within an inferior vena cava, wherein the proximal fixing member is at a proximal end of the proximal segment of the connecting tube;
   wherein the distal segment of the connecting tube comprises only a single pre-determined natural bend, wherein the single pre-determined natural bend of the distal segment is not the predetermined natural bend of the distal fixing member.

2. The device of claim 1, wherein the connecting tube comprises a lumen for a guidewire.

3. The device of claim 1, wherein the distal fixing member comprises:
   a first fixing member body; and
   a plurality of first fixtures for the pulmonary artery radially coupled to the first fixing member body, and
   wherein the proximal fixing member comprises:
   a second fixing member body; and
   a plurality of second fixtures for the inferior vena cava radially coupled to the second fixing member body.

4. The device of claim 3, wherein the first fixing member body or the second fixing member body is configured in a cylindrical shape having a hole in a central axis thereof and coupled to the connecting tube.

5. The device of claim 4, wherein the second fixing member body comprises a protruding hook for the inferior vena cava, the protruding hook being coupled to a lower surface of the second fixing member body.

6. The device of claim 3, wherein the first fixing member body or the second fixing member body is configured in a ring shape, and the distal fixing member or the proximal fixing member comprises a fixing-member-connecting wire having one end thereof coupled to the first fixing member body and inserted into the connecting tube, and having another end thereof coupled to the second fixing member body.

7. The device of claim 1, wherein the distal fixing member comprises:
   a first fixture for the pulmonary artery formed of a wire having a ribbon shape; and
   a first fixing member body coupled to one end of the first fixture, and
   wherein the proximal fixing member comprises:

a second fixture formed of the wire having the ribbon shape; and a second fixing member body coupled to one end of the second fixture.

8. The device of claim 7, wherein the first fixing member body or the second fixing member body is configured in a cylindrical shape having a hole in a central axis thereof and coupled to the connecting tube.

9. The device of claim 7, wherein the first fixing member body or the second fixing member body is configured in a ring shape, and the distal fixing member or the proximal fixing member comprises a fixing-member-connecting wire having one end thereof coupled to the distal fixing member and inserted into the connecting tube, and having another end thereof coupled to the proximal fixing member.

10. The device of claim 1, wherein the blocking part comprises:

a supporting wire having both ends thereof coupled to the connecting tube; and a blocking membrane having one side thereof fixed to the connecting tube and supported by the supporting wire.

11. The device of claim 1, wherein the blocking part is a blocking balloon in a balloon shape capable of expanding or contracting, and the blocking part further comprises:

a balloon tube having a first end thereof connected to and communicated with the blocking balloon; and a balloon-adjusting hub connected to a second end of the balloon for expanding or contracting the blocking balloon.

12. The device of claim 1, wherein the blocking part comprises:

a ring-shaped wire installed to make the connecting tube to be passed through thereof and having a central axis thereof obliquely formed with respect to the connecting tube; and a blocking membrane connecting the connecting tube and the ring-shaped wire to each other.

13. The device of claim 1, further comprising a sheath tube, wherein the connecting tube, blocking part, distal fixing member, and proximal fixing member are contained inside the sheath tube.

* * * * *